US006903339B2

(12) United States Patent
Shelley et al.

(10) Patent No.: US 6,903,339 B2
(45) Date of Patent: Jun. 7, 2005

(54) METHOD OF MEASURING THICKNESS OF AN OPAQUE COATING USING INFRARED ABSORBANCE

(75) Inventors: Paul H. Shelley, Lakewood, WA (US); Diane R. LaRiviere, Seattle, WA (US)

(73) Assignee: The Boeing Company, Seattle, WA (US)

( * ) Notice: Subject to any disclaimer, the term of this patent is extended or adjusted under 35 U.S.C. 154(b) by 193 days.

(21) Appl. No.: 10/304,640

(22) Filed: Nov. 26, 2002

(65) Prior Publication Data

US 2004/0099807 A1 May 27, 2004

(51) Int. Cl.⁷ .............................................. G01N 21/35
(52) U.S. Cl. .................................................. 250/339.01
(58) Field of Search ................................... 250/339.01

(56) References Cited

U.S. PATENT DOCUMENTS

| | | | |
|---|---|---|---|
| 3,017,512 A | | 1/1962 | Wolbert |
| 3,631,526 A | * | 12/1971 | Brunton ................. 250/339.11 |
| 3,693,025 A | | 9/1972 | Brunton |
| 3,973,122 A | | 8/1976 | Goldberg |
| 3,994,586 A | | 11/1976 | Sharkins et al. |
| 4,549,079 A | | 10/1985 | Terasaka et al. |
| 4,791,296 A | | 12/1988 | Carpio |
| 4,800,279 A | | 1/1989 | Hieftje et al. |
| 5,015,856 A | | 5/1991 | Gold |
| 5,091,647 A | * | 2/1992 | Carduner et al. ...... 250/339.09 |
| 5,289,266 A | | 2/1994 | Shih et al. |
| 5,358,333 A | | 10/1994 | Schmidt et al. |
| 5,381,228 A | | 1/1995 | Brace |
| 5,795,394 A | | 8/1998 | Belotserkovsky et al. |
| 6,052,191 A | | 4/2000 | Brayden, Jr. et al. |
| 6,441,375 B1 | * | 8/2002 | Joseph et al. .......... 250/339.09 |

FOREIGN PATENT DOCUMENTS

| | | |
|---|---|---|
| EP | 1 128 178 A1 | 8/2001 |
| EP | 1 233 261 A1 | 8/2002 |
| WO | WO 01/92820 A1 | 12/2001 |

OTHER PUBLICATIONS

Kumar, C. Siva et al., "Studies on anodic oxide coating with low absorptance and high emittance on aluminum alloy 2024", Solar Energy Material & Solar Cells 60 (2000) p. 51–57, Received Feb. 22, 1999, received in revised form Apr. 12, 1999, accepted Jun. 1, 1999, www. elsevier.com.

Kumar, C. Siva et al., "Studies on white anodizing on aluminum alloy for space applications", Applied Surface Science 151 (1999) p. 280–286, Received Mar. 20, 1999, accepted May 31, 1999, www.elsevier.nl/locate/apsusc.

Lee, Jen–Jiang et al., Thickness Measurement of Titanium and Titanium Silicide films by Infrared Transmission, J. Vac. Sci. Technol. , 6:5 (Sep/Oct 1988) pp. 1533–1536.

Schram, T., et al., Nondestructive Optical Characterization of Conversion Coatings on Aluminum, J.Electrochem. Soc, 145:8 (Aug. 1998) pp. 2733–2739.

\* cited by examiner

*Primary Examiner*—Constantine Hannaher
(74) *Attorney, Agent, or Firm*—Black Lowe & Graham, PLLC

(57) ABSTRACT

Amount of opaque coating on a substrate is determined. An infrared beam is transmitted into the opaque coating on the substrate. Infrared beams scattered by the opaque coating are collected and detected at a first wavelength and a second wavelength. Infrared energy $I_{c1}$ and $I_{c2}$ of the collected infrared beams at the first and second wavelengths, respectively, are compared with predetermined values of infrared energy $I_{o1}$ and $I_{o2}$ of collected infrared beams at the first and second wavelengths, respectively, that are scattered by a reference substrate without the opaque coating to determine absorbance values A1 and A2 for the opaque coating at the first and second wavelengths, respectively. Absorbance values A1 and A2 at the first and second wavelengths are given by equations $A1 = -\log_{10}(I_{c1}/I_{o1})$ and $A2 = -\log_{10}(I_{c2}/I_{o2})$. A difference A1−A2 is correlated to an opaque coating amount.

22 Claims, 4 Drawing Sheets

METHOD OF MEASURING THICKNESS OF AN OPAQUE COATING USING INFRARED ABSORBANCE

RELATED APPLICATIONS

This patent application is related to a concurrently-filed U.S. patent application Ser. No. 10/304,627, entitled 'Method of Measuring Amount of Chemical Cure and Amount of Surface Contamination Using Infrared Absorbance', which is hereby incorporated by reference.

FIELD OF THE INVENTION

This invention relates generally to measuring coating thickness and, more specifically to measuring thickness of an opaque coating.

BACKGROUND OF THE INVENTION

Surfaces of many different materials are painted in a variety of applications for aesthetic reasons and for inhibiting corrosion of the surface and a substrate underlying the surface. For a number of reasons, it is desirable to determine thickness of the paint applied to the surface.

It may be desired to apply at least a minimum, predetermined thickness of a paint or primer coating on a surface. Optimal adhesion of a paint coating is a function of thickness. Also, applying at least a minimum, predetermined thickness of paint or primer can ensure that underlying visual features on the surface do not appear through, or "bleed through," the coating. This is important for projecting a professional image to customers to instill a feeling of confidence, such as through company signage or commercial airline tail art. This is also important for ensuring that a product, such as a motor vehicle or an airplane, displays a finish expected by the customer.

Further, applying at least a predetermined, minimum thickness of paint or primer can also provide a desired amount of protection from corrosion of the underlying surface and substrate. Many surfaces that are painted are subject to environments that are conducive to corrosion. For example, marine vessels operate in water, and often the water is salt water. Motor vehicles and airplanes often operate in rainy or humid environments. Therefore, it is desirable to provide at least a minimum amount of protection against corrosion.

In some applications, weight is a consideration. For example, it is desirable to minimize weight of an airplane to reduce fuel consumption. However, paint and primer can be a significant factor in weight of a product, such as an airplane. Therefore, it may also be desired in some applications to limit thickness of paint or primer coating on a surface to a maximum, predetermined thickness.

In order to ensure that a minimum, predetermined thickness of paint or primer coating is applied and that a maximum, predetermined thickness of paint or primer coating is not exceeded, it would be desirable to nondestructively determine thickness of a paint or primer coating on a surface. However, currently known nondestructive measurement techniques are limited in their applicability.

For example, eddy current testing is currently used to determine paint thickness on metal substrates. As is known, eddy current testing detects electrical currents, known as eddy currents. As a result, eddy current testing can only be used to determine thickness of paint or primer that is coated onto a surface of a metallic substrate.

As a further example, ultrasound testing is used to determine thickness of a paint or primer coating on a surface of a composite or plastic substrate. However, ultrasound testing is not as reliable as eddy current testing. Further, accuracy of ultrasound testing is reduced for coating thicknesses below $2/1000$ inch ("mils").

Therefore, there is an unmet need in the art for a simple, reliable, nondestructive method for determining paint thickness regardless of the substrate on which the paint is coated.

SUMMARY OF THE INVENTION

The present invention provides a simple and reliable nondestructive method for measurement of the thickness of an opaque coating, such as a coating of paint or primer, on a substrate regardless of the substrate on which the paint or primer is coated. The invention may be employed in an in-line production facility or may be used intermittently as desired. The process may be used to provide a quantitative measurement, such as thickness, or a qualitative measurement, such as a go or no-go result.

A nondestructive method is provided for efficiently determining thickness of an opaque coating, such as paint or primer, on a surface of a substrate. According to one embodiment of the present invention, an infrared beam is transmitted into the opaque coating on the substrate. Infrared beams are scattered by the opaque coating and collected, and are detected at a first wavelength and a second wavelength. Infrared energy $I_{c1}$ of the collected infrared beams at the first wavelength is compared with a predetermined value of infrared energy $I_{o1}$ of collected infrared beams at the first wavelength that are scattered by a reference substrate without the opaque coating to determine an absorbance value A1 for the opaque coating at the first wavelength. Infrared energy $I_{c2}$ of the collected infrared beams at the second wavelength is compared with a predetermined value of infrared energy $I_{o2}$ of collected infrared beams at the second wavelength that are scattered by the reference substrate without the opaque coating to determine an absorbance value A2 for the opaque coating at the second wavelength. Infrared absorbance values A1 and A2 at the two wavelengths are calculated according to the relationships $A1=-\log_{10}(I_{c1}/I_{o1})$ and $A2=-\log_{10}(I_{c2}/I_{o2})$. A difference between the absorbance values A1 and A2 is calculated, and the thickness of the opaque coating is proportional to the difference between the absorbance values A1 and A2. A calibration performed with traditionally measured thickness standards yields a correlation from which opaque coating thickness can be derived from infrared absorbance measurements on production parts.

BRIEF DESCRIPTION OF THE DRAWINGS

The preferred and alternative embodiments of the present invention are described in detail below with reference to the following drawings.

DETAILED DESCRIPTION OF THE INVENTION

Figure 1:
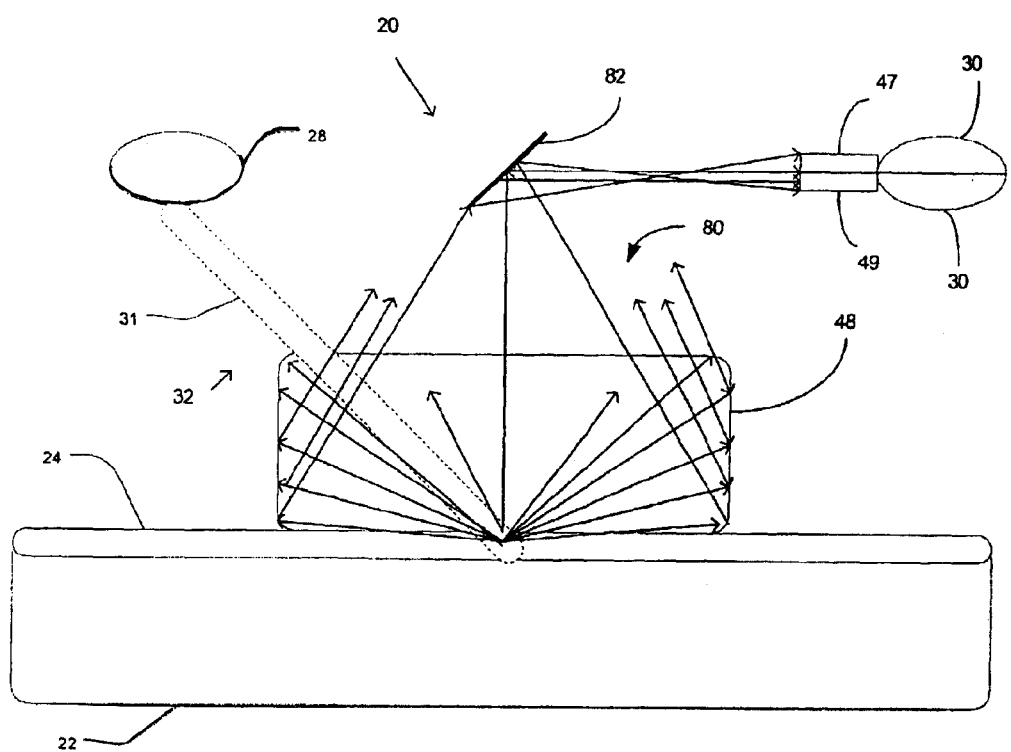
FIG. 1 is a side view of a testing setup.

The present invention provides a method for nondestructively determining thickness of an opaque coating, such as paint or primer, on a substrate by correlating a difference between infrared absorbance of the opaque coating at two predetermined wavelengths to the thickness of the opaque coating regardless of the substrate. By way of overview and with reference to FIG. 1, one presently preferred embodiment of the present invention determines thickness of an opaque coating using a testing setup 20. Initially, a base reference value of infrared energy reflected by a scattering reference substrate with no coating is determined as follows. An infrared transmission beam 31 is transmitted from an infrared source 28 along a predetermined incident beam path 32 and into a diffuse reflectance collector 48 that is placed in contact with the scattering reference substrate. The infrared beam 31 is scattered by the scattering reference substrate and is collected by the collector 48. Collected infrared beams 80 exit the collector 48, are reflected by a reflector 82, are filtered at different wavelength ranges by a pair of filters 47 and 49, and are detected by a pair of infrared detectors 30. The scattering reference substrate is suitably a rough surface, such as without limitation a zero-sintered gold-coated surface, with particles that are approximately the same size as particles of the opaque coating to be measured. A substrate 22 with a sample of an opaque coating 24, such as paint or primer, is put into contact with the collector 48 and the infrared beam 31 is transmitted into the collector 48 as described above. The infrared beam 31 is scattered by the opaque coating 24 and is collected by the collector 48. Collected infrared beams 37 exit the collector 48, are reflected by the reflector 82, are filtered at the different wavelength ranges by the pair of filters 47 and 49, and are detected by the pair of infrared detectors 30. A comparison is made of the infrared energy of the collected infrared beams 80 scattered by the coating 24 and the infrared energy of the base reference value to determine two different absorbance values. A difference between these absorbance values is correlated to absorbance values of known thicknesses of opaque coatings and the thickness of the opaque coating is determined. Specific details of the testing setup 20 are described with more particularity below.

In one non-limiting embodiment for determining thickness of an opaque coating described herein for illustrative purposes only, the measurement is conducted for a coating 24 of polyurethane paint on a metallic substrate 22, such as paint that is suitably used on aircraft. However, measurements of other opaque coatings 24 such as other paints and primers, such as without limitation epoxy primers, latex paint, enamel paint, filled stains and varnishes, and the like, and other substrates 22, such as composites or plastics, wood, fiberglass, and the like, are considered within the scope of this invention. In order to measure the thickness of other opaque coatings 24 that are not illustrated herein, one simply selects suitable wavelength infrared absorbance bands that change with each different material used for the opaque coating 24.

In one present embodiment, the testing setup 20 is suitably a simple infrared filter spectrometer system, including the infrared source 28, infrared beam optics, the collector 48 that contacts the sample or coating 24, the reflector 82, the filters 47 and 49, the detector 30, and a data system (not shown). A non-limiting example of a simple infrared filter system is a Coating Weight Reader produced by Personal Instruments. However, it will be appreciated that other infrared systems are employable with the testing setup 20, such as, without limitation, standard Fourier transform infrared spectrometers and infrared imaging systems. Non-limiting examples of standard Fourier transform infrared spectrometers are a Thermo Nicolet 760 FT-IR spectrometer system fitted with a diffuse reflectance collector accessory and a Surface Optics Corporation SOC400 portable FT-IR spectrometer with a diffuse reflectance collector attachment.

Non-limiting examples of infrared imaging systems employable with the present invention include ImageMax® produced by Thermo Nicolet. It will be appreciated that the various infrared systems may be as used in-line production elements or may be a portable, hand-held arrangement.

In one present embodiment, the infrared beam 31 is suitably transmitted as a broadband mid-infrared light beam (2.5 to 25 microns typically). In one exemplary embodiment, the collected beams 80 are suitably filtered by the pair of filters 47 and 49 at two different wavelength bands. In one exemplary embodiment, the wavelength bands have center wavelengths of approximately 3.0 microns ($\mu$m) and 2.6 microns ($\mu$m). In another exemplary embodiment, the wavelength bands have center wavelengths of approximately 3.0 $\mu$m and 3.3 microns $\mu$m. In these exemplary embodiments, an absorbance peak for the 3.0 $\mu$m wavelength band corresponds to a hydrogen-oxygen peak that exists for polymeric material in most paints, such as without limitation topcoat and primer. As will be discussed in detail below, an absorbance peak for the polymeric material in most paints is not expected at the 2.6 $\mu$m band or the 3.3 $\mu$m band. It will be appreciated that the filters 47 and 49 may act on either the transmitted beam 31 or the collected beams 80. It will be further appreciated that an optimal wavelength for a desired application may deviate from the exemplary wavelength discussed above depending on the material to be measured. Wavelength ranges from about 2.9 $\mu$m to about 3.1 $\mu$m and from either about 2.6 $\mu$m to about 2.7 $\mu$m or about 3.3 $\mu$m to about 3.4 $\mu$m have been found to provide acceptable infrared absorbance characteristics and are to be considered within the scope of this invention for this non-limiting example regarding measurement of amount of polymeric paints such as topcoat and primer. Further, it will be appreciated that when using either standard infrared spectrometer or infrared imaging systems, the filters 47 and 49 may suitably be implemented by hardware or software performing the same filtering function. When the detected infrared beams 80 have wavelength bands within these disclosed ranges, a relationship has been found to exist between a difference between infrared absorbance of the 3.0 $\mu$m band and infrared absorbance of either the 2.6 $\mu$m band or the 3.3 $\mu$m band and the thickness of polymeric paints such as topcoat and primer. However, it will be appreciated that thickness of other opaque coatings may be measured using other wavelength bands that include one wavelength band at which infrared absorbance is expected and another wavelength band at which infrared absorbance is not expected.

Figure 2:
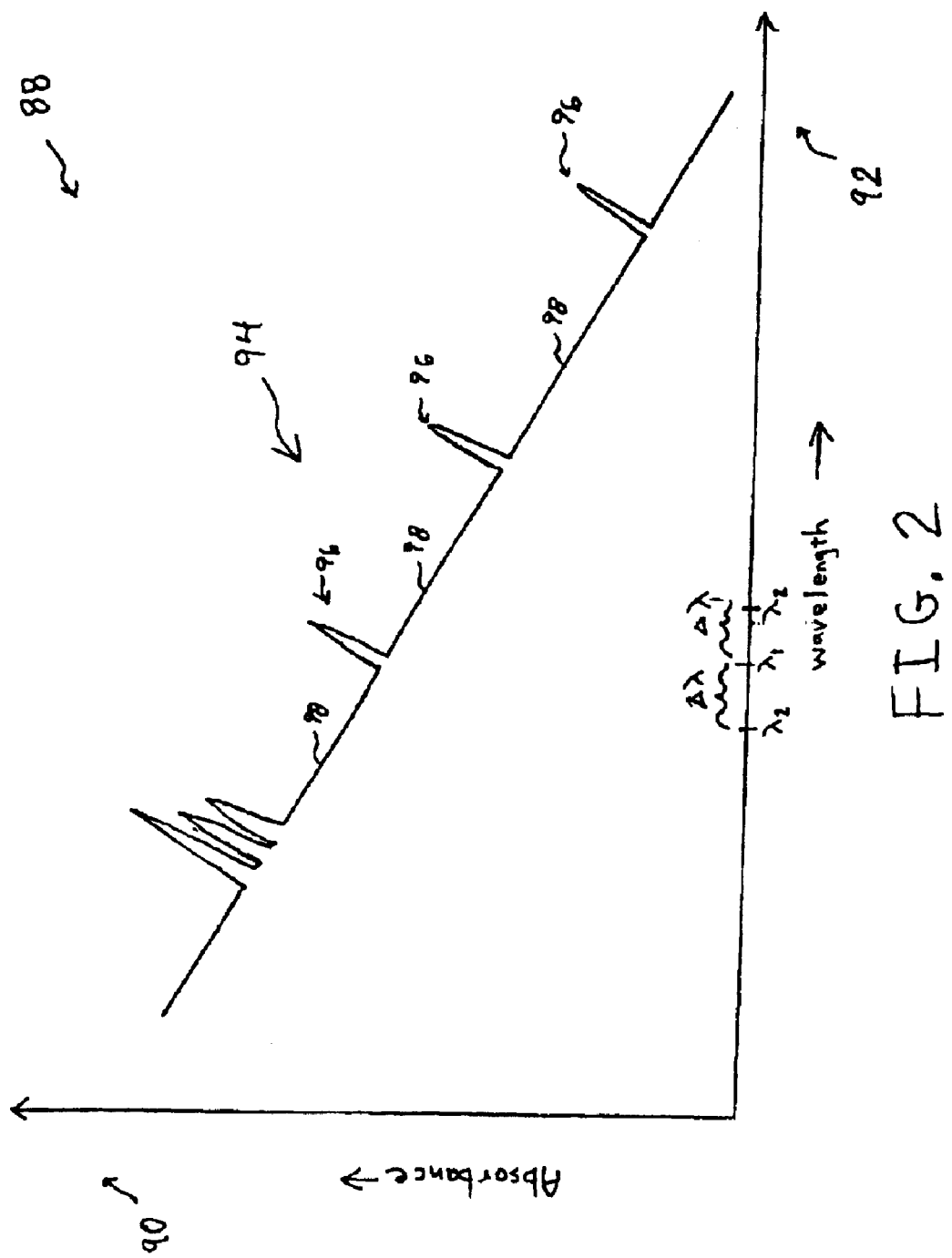
FIG. 2 is a graph of absorbance versus frequency.

According to the present invention, measurement of thickness of the opaque coating takes advantage of changes in scattering as wavelength of infrared radiation varies. Referring now to FIG. 2, a graph 88 shows a curve 94 of absorbance of infrared energy in an opaque coating 24 along a Y-axis 90 versus wavelength along an X-axis 92. As wavelength decreases, wavelength of the infrared energy becomes comparable to size of particles within the opaque coating 24. As a result, scattering increases. Because total reflectance remains constant, an increase in scattering results in a decrease in specular reflectance and absorbance values increase. Conversely, as wavelength increases, wavelength of the infrared energy becomes less comparable to size of particles within the opaque coating 24. As a result, scattering decreases. Because total reflectance remains constant, a decrease in scattering results in an increase in specular reflectance. Accordingly, detection of infrared energy of the specular component of reflected infrared energy increases and absorbance values decrease. Therefore, the curve 94 has a negative slope as wavelength increases.

Advantageously, the present invention measures the specular component of reflected infrared energy at two wavelengths to compensate for changes in specular reflection due to changes in scattering. Absorbance peaks 96 are detected at a first wavelength $\lambda_1$ for the sample being measured. The first wavelength $\lambda_1$ occurs where absorbance is expected for the sample being measured. As discussed above, magnitude of the absorbance of the specular component decreases as wavelength increases. However, the magnitude of the absorbance peaks 96 relative to a baseline 98 (where no absorbance in the sample being measured is expected) remains unaffected by scattering. Therefore, according to the invention, energy of the specular component is additionally detected at a second wavelength $\lambda_2$ where absorbance is not expected for the sample being measured. The second wavelength $\lambda_2$ is offset from the first wavelength $\lambda_1$ by a wavelength difference $\Delta\lambda$. It will be appreciated that the second wavelength $\lambda_2$ is suitably greater than the first wavelength $\lambda_1$ or is suitably less than the first wavelength $\lambda_1$, as desired for a particular application. Advantageously, comparing magnitude of the absorbance peak 96 at the first wavelength $\lambda_1$ to magnitude of absorbance at the second wavelength $\lambda_2$ compensates for the negative slope of the curve 94 due to scattering.

Referring back to FIG. 1, the broadband infrared beam 31 is generated by the infrared source 28. The infrared source 28 is any acceptable source of infrared energy known in the art that can produce the infrared beam 31 having the desired wavelength region. One suitable example of a preferred embodiment of the infrared source is the ReflectIR-P1N source made by Ion Optics.

The infrared detectors 30 in the filtered systems described here are suitably arranged to detect the collected beams 80. One suitable example of the infrared detectors 30 is an Eltec Corp 406MAY-XXX where XXX indicates the filters that are used with the detectors 30.

The diffuse reflectance collector 48 is suitably any acceptable reflectance collector known in the art. Given by way of non-limiting example, the diffuse reflectance collector is suitably a barrel ellipse diffuse reflectance collector, such as, without limitation, a diffuse reflection head available from Surface Optics Corp. The particles within the opaque coating 24 scatter infrared beams 80 at a variety of random angles. Advantageously, the diffuse reflectance collector 48 detects the scattered infrared beams 80 from the variety of random angles, collects the scattered infrared beams 80, and sends the scattered infrared beams 80 to a focal point.

Advantageously, the reflector 82 is placed at approximately the focal point of the diffuse reflectance collector 48. The reflector is placed at a suitable angle to reflect the collected scattered infrared beams 80 toward the detectors 47 and 49. The reflector 82 is suitably any reflector surface having acceptable reflective properties, such as a mirror, any highly-polished surface, or the like.

It will be appreciated that the setup 20 is not depicted to scale in FIG. 1; rather, the diffuse reflectance collector 48 and the reflector 82 are shown greatly enlarged to clearly depict raypaths of the infrared beams 31 and 80.

Figure 3:
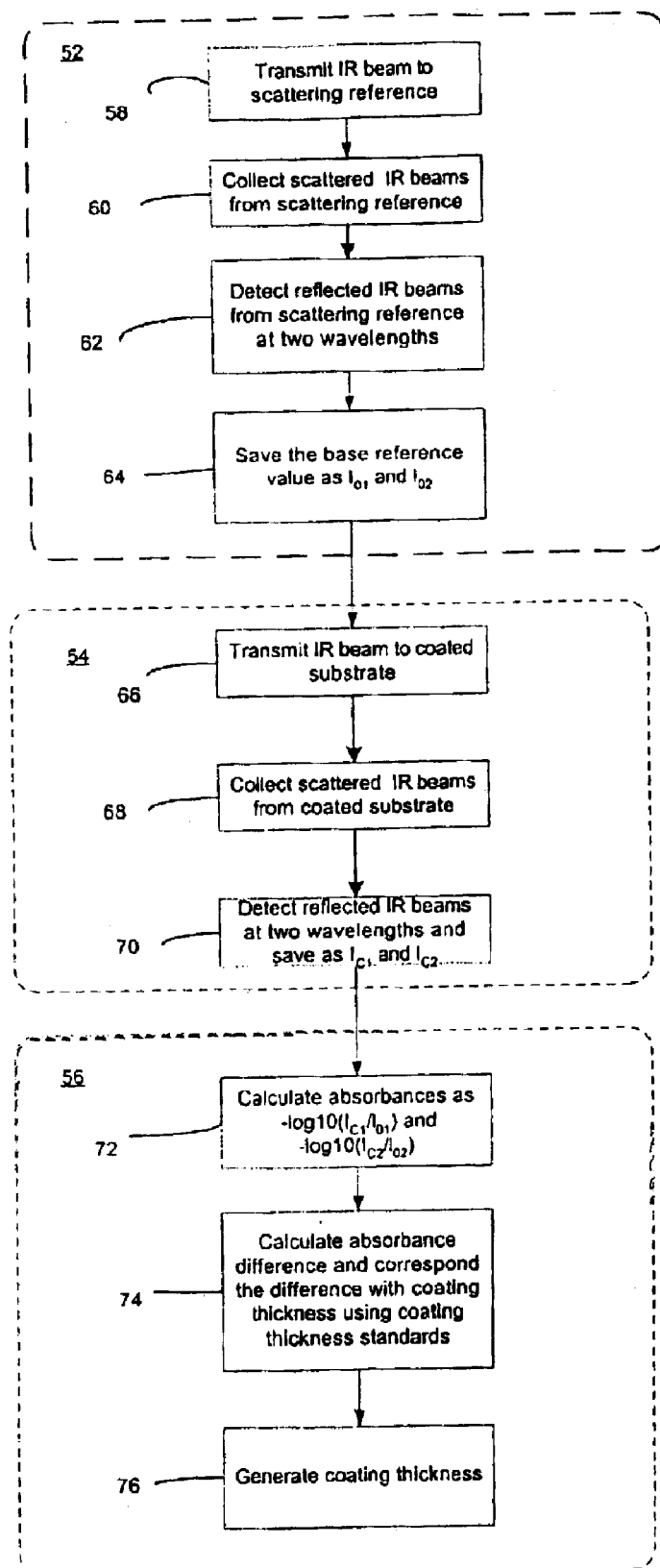
FIG. 3 is a flow chart of a testing process.

Referring now to FIGS. 1 and 3 and given by way of non-limiting example, a process 50 for determining the thickness of a polyurethane paint is illustrated. This process is substantially the same for a filtered infrared beam system, a standard infrared spectrometer system, or infrared imaging systems. Infrared energy base reference values $I_{o1}$ and $I_{o2}$ are determined at a block 52 for a scattering reference. This block determines an amount of infrared energy being scattered without the opaque coating 24 contacting the collector 48. At a block 58, the infrared beam 31 is transmitted to the scattering reference substrate. At a block 60, the infrared beams 80 scattered by the scattering reference substrate are collected by the diffuse reflectance collector 48. At a block 62, the collected scattered beams 80 exiting the collector 48 are reflected by the reflector 82 toward the filters 47 and 49, are filtered at two different wavelengths as discussed above, and are detected by the two detectors 30 to yield the two base reference values of infrared energy $I_{o1}$ and $I_{o2}$. At a block 64 the reference infrared energy values are saved as $I_{o1}$ and $I_{o2}$.

After determining the base reference values $I_{o1}$ and $I_{o2}$, data collection on material coated with the opaque coating 24 begins at a block 54. The diffuse reflectance collector 48 is suitably placed in close physical proximity or, alternately, in physical contact with the opaque coating 24. It will be appreciated the invention advantageously measures thickness of opaque coatings that may be either wet or dry. It would not be desired to place the collector 48 in physical contact with a wet coating because this will change the thickness of the wet coating. At a block 66, the infrared beam 31 is transmitted into the collector 48 and is scattered by particles of the opaque coating 24 as discussed above. At a block 68, the diffuse reflection collector 48 collects the scattered infrared beams 80 and focuses them at a focal point. In this embodiment, the reflector 82 is located toward the focal point of the collector 48 and is positioned to reflect the infrared beams 80 toward the detectors 47 and 49. At a block 70, the infrared beams 80 that are reflected by the reflector 82 are filtered by the pair of filters 47 and 49 and detected by the pair of detectors 30. Values of the infrared energy of the attenuated beam detected at the two wavelengths are saved as infrared energies $I_{c1}$ and $I_{c2}$. It will be appreciated that parameters such as the angle at which the incident beam 31 enters the collector 48 and overall incident beam path length are maintained substantially similar in both reference value determination and thickness determination to limit potential errors.

Data calculation and compilation occurs at a block 56. The data compilation process includes calculation at a block 72 of absorbance values A1 and A2 at the first and second wavelengths according to the relationships $A1 = -\log_{10}(I_{c1}/I_{o2})$ and $A2 = -\log_{10}(I_{c2}/I_{o2})$. At a block 74 a difference between A1 and A2 is calculated. That is, A2 is subtracted from A1. An absorbance difference of A1–A2 is preferably calculated (rather than an absorbance ratio of A1/A2) because the magnitude of A2 may often be at or near zero. It will be appreciated that division by a denominator term at or near zero would return an undefined result. By preferably calculating an absorbance difference rather than an absorbance ratio, the present invention advantageously avoids a possibility of an undefined result by avoiding a possibility of division by a denominator term at or near zero.

The compilation and calculation is suitably performed in a number of acceptable manners. For example, in one embodiment, it is performed by a processor or microprocessor (not shown) arranged to perform mathematical operations. Any processor known in the art is acceptable such as, without limitation, a Pentium®-series processor available from Intel Corporation or the like. The processor is suitably included within the infrared spectrometer and is also suitably provided as a stand-alone unit that is electrically connected to receive data from the infrared detectors 30. Alternately, the calculation is performed by an electronic computer chip or is performed manually. The results of the calculation yield an absorbance difference A1–A2 that corresponds to the thickness of the opaque coating 24.

At a block 76, the coating thickness is generated. The absorbance difference measurement is repeated for many different thicknesses of different opaque coatings with a sample system that is made as a standard for the type of opaque coating to be measured. More specifically, a calibration is calculated for the thickness by generating a plot or linear regression of thickness values versus absorbance ratio values. This calibration can then be used to calculate thickness directly from absorbance difference values.

The opaque coating applied to each standard to be measured for the calibration data is carefully applied and measured with an alternative method after the absorbance values are measured. An example of an acceptable alternative method includes cutting a painted sample, such as a small sample of around one square inch, and polishing the edges of the sample. Thickness of the coating of the sample is measured directly by measuring thickness of the edges with a calibrated microscope. If desired, more than one edge may be measured and the edge measurements are averaged. An example of another acceptable alternative method includes weighing the standard, measuring the absorbance values of the standard, removing the opaque coating with a solvent, and weighing the standard again. The coating amount for the standard is calculated in terms of milligrams per square foot ($mg/ft^2$) and is converted to a thickness measurement, and a calibration plot or regression is made using several standards.

Figure 4:
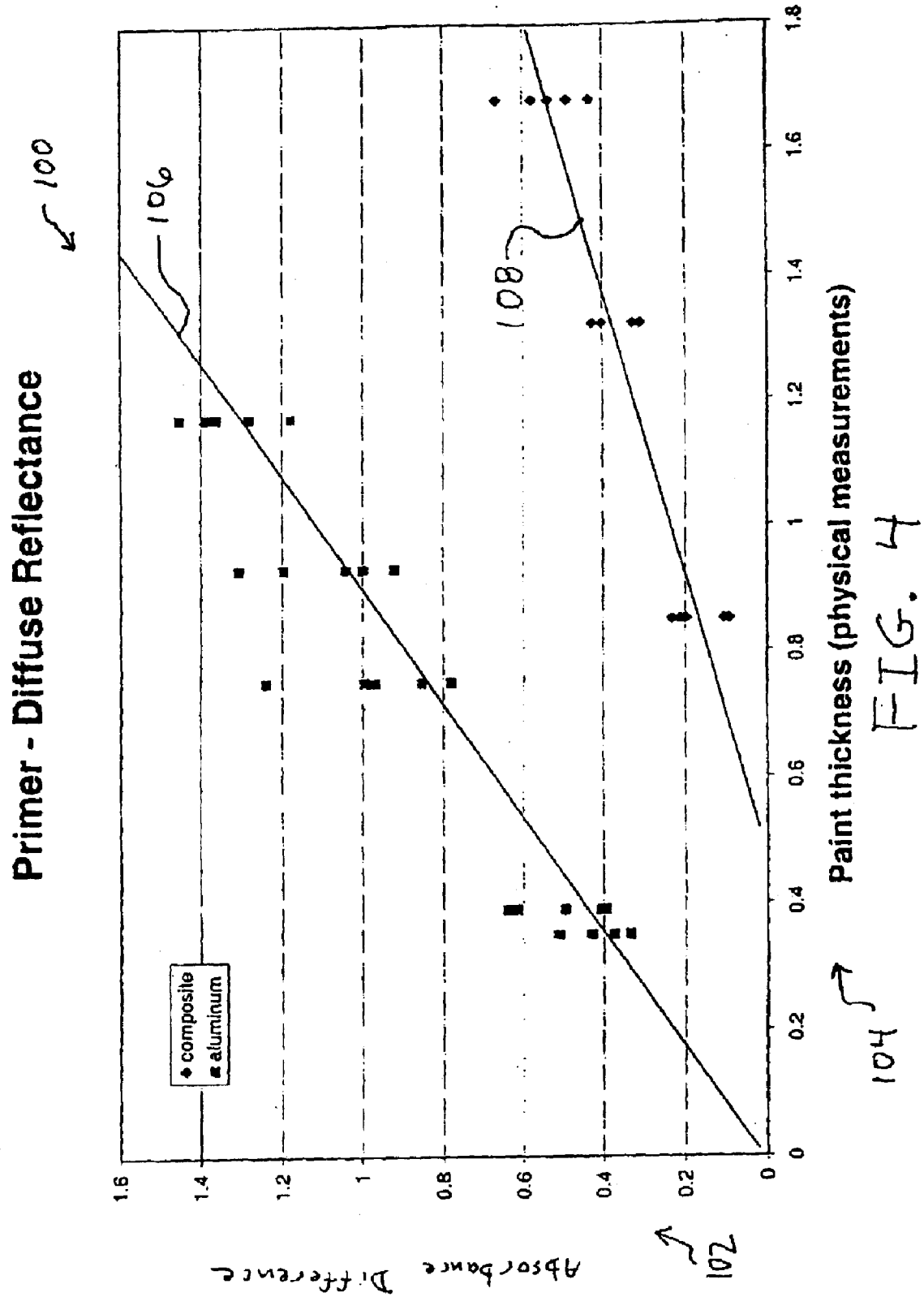
FIG. 4 is a graphical illustration of the relation between paint thickness and infrared absorbance.

FIG. 4 depicts test data illustrating correlation between thickness of an opaque coating and infrared absorbance difference at the preferred wavelengths. It will be appreciated that FIG. 4 represents experimental data generated by a bench-top FTIR infrared spectrometer. However, each trial was performed by the process of the present invention. It will also be appreciated that prior to testing, a reference determination using a scattering reference substrate was made according to the present invention. A graph 100 shows infrared absorbance difference along a Y-axis 102 versus thickness of an opaque coating along an X-axis 104. A curve 106 plots infrared absorbance difference versus thickness of an epoxy primer coating on a 2024 aluminum alloy substrate. A curve 108 plots infrared absorbance difference versus thickness of an epoxy primer coating on a graphite and epoxy composite substrate.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

What is claimed is:

1. A non-destructive method of determining an amount of opaque coating on a substrate, the method comprising:

non-destructively determining a value A1 of absorbance of infrared energy at a first wavelength in an opaque coating on a substrate, wherein the value A1 is a selected function of a ratio that includes a value $I_{c1}$ of infrared energy at the first wavelength that is scattered by the opaque coating divided by a value $I_{o1}$ of infrared energy at the first wavelength that is scattered by a reference substrate without the opaque coating;

non-destructively determining a value A2 of absorbance of infrared energy at a second wavelength in the opaque coating on the substrate, wherein the value A2 is a selected function of a value $I_{c1}$ of infrared energy at the first wavelength that is scattered by the opaque coating divided by a value $I_{c2}$ of infrared energy at the second wavelength that is scattered by the opaque coating; and correlating a difference A1–A2 to an amount of the opaque coating.

2. The method of claim 1, wherein non-destructively determining the value A1 is calculated according to the equation $A1=-\log_{10}(I_{c1}/I_{o1})$; and Wherein non-destructively determining the value A2 is calculated according to the equation $A2=-\log_{10}(I_{c2}/I_{o2})$.

3. The method of claim 1, wherein the opaque coating includes paint.

4. The method of claim 1, wherein the amount includes thickness.

5. A non-destructive method of determining an amount of opaque coating on a substrate, the method comprising:

transmitting an infrared beam into an opaque coating on a substrate;

collecting scattered infrared beams that are scattered by the opaque coating;

detecting the collected infrared beams at a first wavelength and a second wavelength that is different from the first wavelength;

comparing infrared energy $I_{c1}$ of the collected infrared beams at the first wavelength with a predetermined value of infrared energy $I_{o1}$ of collected infrared beams at the first wavelength that are scattered by a reference substrate without the opaque coating to determine an absorbance value A1 for the opaque coating at the first wavelength, wherein the value A1 is a selected function of a ratio of $I_{c1}$ and $I_{o1}$;

comparing infrared energy $I_{c2}$ of the collected infrared beams at the second wavelength with a predetermined value of infrared energy $I_{o2}$ of collected infrared beams at the second wavelength that are scattered by the reference substrate without the opaque coating to determine an absorbance value A2 for the opaque coating at the second wavelength, wherein the value A2 is a selected function of a ratio of $I_{c2}$ and $I_{o2}$; and correlating a difference A1–A2 to an opaque coating amount.

6. The method of claim 5, wherein the opaque coating includes paint.

7. The method of claim 5, wherein the amount includes thickness.

8. The method of claim 5, wherein the substrate is metallic.

9. The method of claim 5, wherein the substrate includes one of a composite and a plastic.

10. The method of claim 5, wherein the first wavelength is in a range from about 2.9 μm to about 3.1 μm.

11. The method of claim 5, wherein the second wavelength is in a range from about 2.6 μm to about 2.7 μm.

12. The method of claim 5, wherein the second wavelength is in a range from about 3.3 μm to about 3.4 μm.

13. The method of claim 5, wherein the absorbance values A1 and A2 are calculated according to the equations $$A1=-\log_{10}(I_{c1}/I_{o1}); \text{ and}$$

$$A2=-\log_{10}(I_{c2}/I_{o2}).$$

14. A non-destructive method of determining an amount of opaque coating on a substrate, the method comprising:

transmitting an infrared beam into an opaque coating on a substrate;

collecting with a diffuse reflectance collector scattered infrared beams that are scattered by the opaque coating;

filtering the collected infrared beams at a first wavelength and a second wavelength that is different from the first wavelength;

detecting the filtered collected infrared beams at the first wavelength and the second wavelength;

comparing infrared energy $I_{c1}$ of the collected infrared beams at the first wavelength with a predetermined value of infrared energy $I_{o1}$ of collected infrared beams at the first wavelength that are scattered by a reference substrate without the opaque coating to determine an absorbance value A1 for the opaque coating at the first wavelength, wherein the value A1 is a selected function of a ratio of $I_{c1}$ and $I_{o1}$;

comparing infrared energy $I_{c2}$ of the collected infrared beams at the second wavelength with a predetermined value of infrared energy $I_{o2}$ of collected infrared beams at the second wavelength that are scattered by the reference substrate without the opaque coating to determine an absorbance value A2 for the opaque coating at the second wavelength, wherein the value A2 is a selected function of a ratio of $I_{c2}$ and $I_{o2}$; and correlating a difference A1−A2 to an opaque coating amount.

15. The method of claim 14, wherein the opaque coating includes paint.

16. The method of claim 14, wherein the amount includes thickness.

17. The method of claim 14, wherein the substrate is metallic.

18. The method of claim 14, wherein the substrate includes one of a composite and a plastic.

19. The method of claim 14, wherein the first wavelength is in a range from about 2.9 µm to about 3.1 µm.

20. The method of claim 14, wherein the second wavelength is in a range from about 2.6 µm to about 2.7 µm.

21. The method of claim 14, wherein the second wavelength is in a range from about 3.3 µm to about 3.4 µm.

22. The method of claim 14, wherein the absorbance values A1 and A2 are calculated according to the equations $$A1 = -\log_{10}(I_{c1}/I_{o1}); \text{ and}$$

$$A2 = -\log_{10}(I_{c2}/I_{o2}).$$

\* \* \* \* \*